(12) United States Patent
Woerner

(10) Patent No.: US 7,214,481 B2
(45) Date of Patent: May 8, 2007

(54) CHARCOAL STABILIZATION OF PHENYL PHOSPHATES

(75) Inventor: Thomas M. Woerner, Westminster, MD (US)

(73) Assignee: BioFX Laboratories, Inc., Owings Mills, MD (US)

( * ) Notice: Subject to any disclaimer, the term of this patent is extended or adjusted under 35 U.S.C. 154(b) by 0 days.

(21) Appl. No.: 11/262,715

(22) Filed: Nov. 1, 2005

(65) Prior Publication Data

US 2006/0063220 A1 Mar. 23, 2006

Related U.S. Application Data

(62) Division of application No. 10/727,537, filed on Dec. 5, 2003, now Pat. No. 7,001,717.

(51) Int. Cl.
*C12Q 1/00* (2006.01)

(52) U.S. Cl. .............. 435/4; 435/21; 435/183; 436/8; 436/145; 436/146; 436/176

(58) Field of Classification Search ..................... None
See application file for complete search history.

(56) References Cited

U.S. PATENT DOCUMENTS

| 1,958,210 A | 5/1934 | Scott |
| 3,951,859 A | 4/1976 | Inaba et al. |
| 4,029,593 A | 6/1977 | Schäpel et al. |
| 4,042,335 A | 8/1977 | Clément |
| 4,132,598 A | 1/1979 | Modrovich |
| 4,372,874 A | 2/1983 | Modrovich |
| 5,464,560 A | 11/1995 | Schilling et al. |
| 5,895,819 A | 4/1999 | Hagi |
| 5,948,631 A | 9/1999 | Nagel et al. |
| 2002/0058279 A1 | 5/2002 | Fritsch et al. |

OTHER PUBLICATIONS

Siegenthaler, E, "Phosphatase test with sodium p-nitrophenyl phosphate" Mitteilungen Aus Der Gebiete Der Lebensmitteluntersuchung Und Hygiene, 1959, vol. 47, translation provided.
HowStuffWorks, "What is activated charcoal and why is it used in filters?" http://www.howstuffworks.com/question 209.htm accessed Nov. 3, 2004.
Sigma-Aldrich Product Catalogue, "2-Amino-2-methyl-1,3-propanediol" (AMPD), 2004, http://www.sigmaaldrich.com/cgi-bin/hsrun/Suite7/Suite/Suite.hjx;start=Suite.HsViewHierarchy.run?Detail=Product&ProductNumber=SIGMA-A5888&VersionsSequence1, accessed Nov. 3, 2004.
Sigma-Aldrich Product Catalogue, "BIS-TRIS"2004, http://www.sigmaaldrich.com/cgi-bin-hsrun/Suite7/Suite/Suite.hjx;start=Suite.HsViewHierarchy.run?Detail=Product&ProductNumber=SIGMA-B7535&VersionsSequence1, accessed Nov. 3, 2004.

*Primary Examiner*—Leon B. Lankford, Jr.
*Assistant Examiner*—Allison M. Ford
(74) *Attorney, Agent, or Firm*—Buchanan Ingersoll & Rooney

(57) ABSTRACT

The invention discloses methods, compositions and kits for stabilizing a solubilized phenyl phosphate, preferably paranitrophenyl phosphate (PNPP), using charcoal. Also disclosed are methods, compositions and kits for recycling solubilized phenyl phosphate, preferably PNPP, that has an absorbance of less than 0.1 when measured at 405 nm due to non-enzymatic hydrolysis.

21 Claims, No Drawings

CHARCOAL STABILIZATION OF PHENYL PHOSPHATES

This application is a divisional of U.S. patent application Ser. No. 10/727,537 now U.S. Pat. No. 7,001,717, filed on Dec. 5, 2003, hereby incorporated by reference in its entirety.

FIELD OF THE INVENTION

The invention relates to phosphate-containing enzyme substrate compositions that have improved stability and methods for producing these stable enzyme substrate compositions. The enzyme substrates may be included in a reagent kit for an enzyme activity assay and the like. A preferred example are p-nitrophenyl phosphate (PNPP) compositions that have improved stability and methods and compositions for stabilizing and recycling PNPP.

BACKGROUND OF THE INVENTION

The determination of hydrolase activity, in particular alkaline phosphatase and acid phosphatase activity, in human body fluid is clinically very important. Substrates containing aromatic organic groups and hydrolizable phosphoric esters are typically used as the substrates of these hydrolases. These substrates include, phenyl phosphates, such as paranitrophenylphosphate (PNPP), 4-methylumbelliferone phosphoric acid (4MUP), o-cresolphthalein monophosphate disodium salt, phenylphthalein, and isomers and salts thereof. The hydrolase enzymes, in particular alkaline phosphatase and acid phosphatase, can be found in blood serum and measurement of these enzymes may be used to detect a variety of abnormal conditions.

Alkaline and acid phosphatases are widely distributed in nature and their properties have been extensively studied. The enzyme catalyzes the hydrolysis of phosphate monoesters:

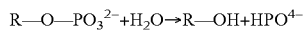

$$R-O-PO_3^{2-} + H_2O \rightarrow R-OH + HPO_4^{2-}$$

Alkaline phosphatase is an enzyme found in all tissues. Tissues with particularly high concentrations include liver, bile ducts, placenta and bone. Since these tissues release enzymes into the blood, the amount of alkaline phosphatase can be measured in samples of blood serum. Increased levels of alkaline phosphatase in blood serum can indicate a variety of conditions, including bone and liver disease.

Acid phosphatase enzyme measurement in blood serum is also highly useful. Acid phosphatase is primarily produced in the prostate gland and is normally found in very small amounts in the blood. Increased levels of acid phosphatase can be an indication of prostatic carcinoma.

The levels of alkaline phosphatase and acid phosphatase can be measured based upon hydrolysis of the substrate paranitrophenylphosphate (PNPP) in the presence of magnesium ions. These phosphatases hydrolyze PNPP to a colored end-product. The rate of hydrolysis can be determined by following the increase in absorbance, which is measured at approximately 405 nm.

Additionally, these enzymes can be used to measure proteins and peptides contained in biological samples (e.g., sera, urine and blood) or in research reactions. For example, these compounds can be used to quantitate the amount of analyte (i.e., nucleic acid, protein or peptide of interest) present in a sample or a reaction. Assays using these phosphatases and the phenyl phosphate substrate include, but are not limited to, sandwich immunoassays, competitive immunoassays, immunoprecipitation reactions assays and enzyme linked immunosorbant assay (ELISA). In particular, the ELISA is a useful and powerful method in estimating the amount of proteins and peptides in serum, urine, culture supernatant, and the like.

The phosphatase enzymes are particularly useful in these assays as they have high affinity for phosphate groups and can be readily measured using substrates with a reactive phosphate group. As described above, substrates containing aromatic organic groups and hydrolyzable phosphoric esters readily can be used to measure the phosphatases. In particular, these enzymes hydrolyze the phenyl phosphate substrate to an end-product that is colored in basic solution.

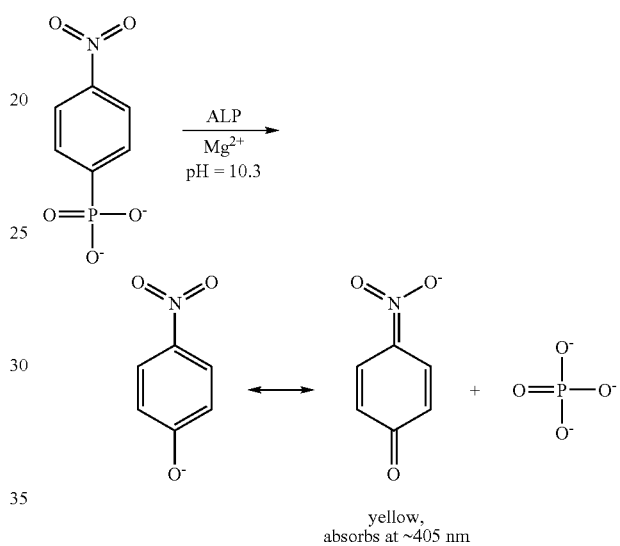

yellow, absorbs at ~405 nm

The rate of hydrolysis can be determined by following the increase in absorbance at approximately 405 nm, in the instance of PNPP. Measurement of the increase in absorbance due to the p-nitrophenoxide in the example of PNPP produced by reaction with the phosphatase enzymes in a given time frame provides a fairly accurate determination of the amount of analyte present.

Originally, many immunoassays relied on radiodetection of the analyte of interest. Due to the hazards and costs related to use of radioisotopes (e.g., radioactive contamination and production of radioactive waste), enzyme-linked or enzyme-based assay technology was developed based on the use of colorimetric assays, using phenyl phosphate agents.

One of the most commonly used colorimetric systems initially for ELISAs was p-nitrophenylphosphate (PNPP)-alkaline phosphatase reaction. Alkaline phosphatase is an extremely stable enzyme, making it commercially very valuable; however, PNPP is extremely unstable. The phosphate group of the PNPP is extremely labile, and PNPP will hydrolyze to the colored phenoxide in solution over time even, in the absence of enzyme. In fact, when left at room temperature in a lighted room in a clear vessel, PNPP will hydrolyze within only a few hours, and even when stored at low temperatures in an amber vessel, PNPP will still hydrolyze over time. The instability of PNPP in solution renders it commercially difficult for research uses, as it is commercially desirable for the enzyme substrates to remain stable for prolonged periods of time. As a result of the problems encountered with PNPP and other phenyl phosphates, there has been a great deal of research into methods for stabilizing phenyl phosphates.

The present commercial state of the art used for stabilizing phenyl phosphates, such as PNPP, is to provide the compounds in a solid matrix, either by freeze drying, dry blending such as used for tableting dried powders in the pharmaceutical, diagnostic and related industries, or chemical immobilization by locking the chemical structure of the substrate in a solid matrix. However, these approaches are expensive, and thus, are not commercially practical. In addition, by providing the phenyl phosphate in dried form, a partial product is being supplied. The end-user must reconstitute the phenyl phosphate introducing quality control problems in the final product and when reconstituted, the phenyl phosphate solution hydrolyzes and cannot be stored for extended periods of time.

Attempts have been made to develop methods for stabilizing reactive phosphoric organic diagnostic reagents, including PNPP, in solution. For example, U.S. Pat. No. 4,132,598 describes methods for stabilizing labile organic diagnostic reagents, including PNPP, in aqueous solution by mixing the solution with a stabilizing agent selected from phenyl and phenylic compounds, imidazol, and nitro aliphatic compounds. U.S. Pat. No. 4,372,874 describes methods for stabilizing labile organic reagents, including PNPP, by dissolving the reagents in a water miscible organic solvent and providing in contact with the solution at least one percent by weight of an inert, high surface area, particulate desiccant.

U.S. Pat. No. 5,895,819 describes stabilizing phosphoric esters using citric acid and/or succinic acid. While it may be possible to stabilize phosphoric esters in acidic solutions, to use the solutions as substrates for phosphatases, the solutions must be buffered to basic pH in which the phosphoric esters are no longer stabilized. U.S. Pat. No. 5,948,631 describes a mixture of N-methylglucamine salt of o-cresolphthalein monophosphoric acid and N-methylglucamine for detecting alkaline phosphatase, the mixture being stable to non-enzymatic hydrolysis.

Although these methods have been developed, none of these methods have proven to be commercially viable and permit long term storage of a phenyl phosphate in solution either at reduced temperatures, such as 4° C., or elevated temperatures, which may be experienced while shipping phenyl phosphate solutions or storing phenyl phosphate solutions on bench-tops in the laboratory. Accordingly, a need continues to exist for improving the storage stability of phenyl phosphate in solution for use as a substrate in diagnostic tests.

SUMMARY OF THE INVENTION

Therefore, notwithstanding what has previously been reported in the literature, there exists a need for improved methods of stabilizing solubilized phenyl phosphates, which are in a ready-to-use forms. Additionally, methods are needed to recycle solubilized phenyl phosphates, which have been converted to a colored product in the absence of enzyme to an otherwise commercially useless form of solubilized phenyl phosphate. The compositions and kits for stabilizing and recycling phenyl phosphate, as described herein, will allow for more consistent laboratory results as they remove the need to prepare a phenyl phosphate solution. In addition, the compositions and kits for stabilizing and recycling phenyl phosphate, as described herein, will permit more consistent background measurements, and will greatly reduce the cost of shipping and handling phenyl phosphate. Furthermore, the compositions and kits for stabilizing and recycling phenyl phosphate, as described herein, allow phenyl phosphate to be provided in ready-to-use and concentrated forms that have increased shelf-life. In accordance with the present invention, it has been found that it is possible to store phenyl phosphate in a buffered solution in the presence of reagents that effectively stabilize the reactive phosphate groups and thus protect the solubilized phenyl phosphate from non-enzymatic hydrolysis or conversion to a colored product. In particular these stabilizing reagents are charcoal, preferably activated charcoal. Although PNPP is the phenyl phosphate exemplified herein, other phenyl phosphates, their salts and isomers are also contemplated for use in the methods, compositions, and kits described herein. Accordingly, all references to PNPP encompass PNPP, other phenyl phosphates, their salts, and isomers thereof.

The present invention is uniquely designed so that the labile ingredients in a liquid reagent solution are effectively "stabilized" or are "recycled" to a state wherein their background absorbance when measured at approximately 405 nm is less than 0.1 while having acceptable activity (absorbance of less than 0.1 is the desirable limit for the background). Absorbance of greater than or equal to 0.2 OD/min is the preferred limit for measuring activity. The means of stabilizing a phenyl phosphate, as described herein, provides long-term stability in a liquid media. Moreover, according to the present invention close tolerance control can be achieved in the manufacturing of a high quality product, that also eliminates the inconvenience of the rigid package size and the high cost of packaging, freezing, freeze drying, frozen storage, and reagent waste. Additionally, the compositions and methods described herein permit long-term storage at temperatures of 4° C. or higher regardless of the lighting and regardless of the color of the container in which the solubilized phenyl phosphate is stored, thus eliminating the need for an amber bottle.

Thus, one aspect of the invention provides for a method for stabilizing a solubilized phenyl phosphate comprising contacting the solubilized phenyl phosphate with a stabilizing amount of charcoal. A preferred phenyl phosphate is paranitrophenyl phosphate (PNPP), but other phosphates are also contemplated, as discussed herein. Preferably, the phenyl phosphate is in an aqueous buffered solution having a pH of greater than approximately 9.0. If PNPP is the phenyl phosphate, then the PNPP can be present in an amount of $\leq 3.0$ g/L PNPP, and more preferably in an amount of approximately 1.0 to 1.5 g/L PNPP. The charcoal in turn can be present in the amount of approximately 5 to 15 mg/mL (e.g., 10 mg/mL). Preferably the charcoal is activated charcoal.

Another aspect of the invention contemplates a kit for phosphatase-phenyl phosphate based reactions, comprising a phosphatase and a stabilized solubilized phenyl phosphate. Preferably, the phenyl phosphate is PNPP, but can be any phenyl phosphate. Yet another object of the invention provides for a method for recycling a solubilized phenyl phosphate (e.g., PNPP) comprising admixing colored, solubilized phenyl phosphate with a recycling amount of charcoal (e.g., an activated charcoal). If PNPP is being recycled, then the concentration of solubilized PNPP is $\leq 3.0$ g/L. The amount of charcoal for stabilizing and recycling PNPP is an amount of approximately 5 to 15 mg/mL (e.g., 10 mg/mL).

In yet another embodiment, the invention contemplates either that the charcoal can remain in solution or can be removed from the solution using any of the methods discussed herein (e.g., centrifugation, chemical extraction and the like).

Another aspect of the invention contemplates a stabilized solubilized phenyl phosphate (e.g., PNPP) comprising a buffer, a phenyl phosphate, and a stabilizing amount of charcoal. Preferably the charcoal is activated charcoal. When the stabilized solubilized phenyl phosphate is PNPP, the PNPP is in an amount of less than 3.0 g/L. The phenyl phosphate can be a $Na^+$ salt, a $Mg^{+2}$ salt, a $NH_4^+$ salt or an isomer thereof. The buffer in which the phenyl phosphate is solubilized is preferably a basic buffer (e.g., DEA, BIS-TRIS, TRIS, AMP, or AMPD). The solubilized, stabilized phenyl phosphate composition can further comprise a magnesium compound.

Yet a further aspect contemplates a ready-to-use enzyme substrate composition comprising a phenyl phosphate (e.g., PNPP or any phenyl phosphate salt or isomer), a buffer (e.g., a basic buffer such as any of those disclosed herein), and charcoal (e.g., activated charcoal).

In another embodiment, a reagent kit for an enzyme activity assay comprising the ready-to-use enzyme substrate composition discussed above and an enzyme is contemplated. The enzyme preferably is alkaline phosphatase or acid phosphatase.

In yet a further aspect a method is contemplated for preparing an aqueous liquid substrate system used in phosphatase enzyme determination comprising:
(a) solubilizing a phenyl phosphate in an aqueous buffered solvent to provide a phenyl phosphate solution;
(b) adding a magnesium compound to the phenyl phosphate solution;
(c) contacting the solution with a stabilizing amount of charcoal; and
(d) sealing the solution.

The phenyl phosphate can be PNPP or another phenyl phosphate salt or isomer.

It is still a further object to provide a vessel for containing solubilized phenyl phosphate in a basic buffer, wherein the vessel comprises charcoal on the surface of the vessel exposed to the solubilized phenyl phosphate.

Another aspect of the invention provides a kit for recycling a solubilized phenyl phosphate having an absorbance over 0.1 OD due to non-enzymatic hydrolysis when measured at 405 nm comprising a stabilizing amount of charcoal. The charcoal is preferably activated and preferably in an amount of 10 mg/mL+/−5 mg/mL if PNPP is being recycled. The kit also contemplates that the charcoal is in a self-contained unit (e.g., a pellet, a tablet, a tablet in a blister pack, contained in dialysis tubing or its equivalent, or a perforated capsule).

DETAILED DESCRIPTION OF THE INVENTION

The present invention relates generally to methods of stabilizing solubilized phenyl phosphate. According to the present invention, solubilized phenyl phosphate is contacted with a stabilizing amount of charcoal. By contacting the solubilized phenyl phosphate with charcoal, a buffered solution of phenyl phosphate can be provided with surprising stability. The stabilized solubilized phenyl phosphate of the present invention is provided in a buffered solution, preferably having a pH of greater than 9.0. According to the present invention, solubilized phenyl phosphate contacted with a stabilizing amount of charcoal may be stable and thus exhibit acceptable background absorbance and activity for 30 days or more when stored on the bench-top at approximately room temperature and exposed to light and for two years or longer when stored at 4° C. in a refrigerator.

The present invention also relates to methods of recycling solubilized phenyl phosphate, which has colored due to non-enzymatic hydrolysis thus becoming commercially useless, to solubilized phenyl phosphate having acceptable activity and background absorbance. By contacting a solubilized phenyl phosphate, which has previously colored due to non-enzymatic hydrolysis, with charcoal, a solubilized phenyl phosphate can be provided having acceptable background absorbance and acceptable activity for use in enzyme assays.

According to the present invention, to provide solubilized phenyl phosphate with excellent stability and to recycle previously colored, solubilized phenyl phosphate, the solubilized phenyl phosphate is contacted with charcoal. The solubilized phenyl phosphate can be stored in contact with the charcoal or in the alternative, the solubilized phenyl phosphate can be contacted with the charcoal for a finite period of time and then substantially all of the charcoal may be removed prior to long-term storage of the solubilized phenyl phosphate.

The following also provides apparatus, compositions and kits for stabilizing and/or recycling solubilized phenyl phosphate.

1. Definitions and Abbreviations

1.1 Definitions

Terms used throughout this application are to be construed with ordinary and typical meaning to those of ordinary skill in the art. However, the following terms are discussed in detail below.

Moreover, for the purposes of the present invention, the term "a" or "an" entity refers to one or more of that entity. For example, "a molecule" or "a buffer" refers to one or more of those compounds or buffers respectively. As such, the terms "a", "an", "one or more" and "at least one" can be used interchangeably herein. It is also to be noted that the terms "comprising", "including" and "having" can be used interchangeably.

By "phenyl phosphate" is meant any phenyl phosphate that can serve as a substrate for a phosphatase. Possible phenyl phosphates include but are not limited to Na salts, $NH_4$ salts, Mg salts, dicyclohexylammonium salt, Di(Tris) salt, and di(2-amino-2-ethyl(1,3-propanediol)) salt as well as isomers thereof. A preferred phenyl phosphate is PNPP.

"PNPP" means any paranitrophenylphosphate or paranitrophenylphosphate-like compound and salts thereof, which can serve as a substrate for an enzyme, such as alkaline and acid phosphatase. PNPP includes salts of PNPP, such as, $Na^+$ and $NH_4^+$ salts and isomers thereof.

"Solubilized phenyl phosphate" means a phenyl phosphate, as provided above, solubilized in an aqueous buffer solution, preferably in a basic buffer. The solubilized phenyl phosphate may also include other solvents, which are miscible with the aqueous solution, including, for example, methanol, propanediol, and the like. The solubilized phenyl phosphate can be in a "ready-to-use" form, wherein no further dilution of the solubilized phenyl phosphate is necessary for use as a substrate in an assay. Alternatively, "solubilized phenyl phosphate" also can refer to concentrated forms of phenyl phosphate, which should be diluted prior to use in an assay (e.g., 3.0 g/L). Preferably, the phenyl phosphate is about 3 g/L or less in a suitable buffer. More preferably, the solubilized phenyl phosphate is about 2 g/L or less. Even more preferably, the solubilized phenyl phosphate is in basic buffer is about 1.0 to about 1.5 g/L (e.g., 1.1, 1.2, 1.3 and 1.4 are all contemplated concentrations).

By a "basic buffer" or "buffer" as used herein is meant buffers with a pH over 7.0. More preferably, the pH of the buffer is over 9.0. Suitable buffers include, but are not limited to, MOPS, HEPES, TES, barbital (also known as barbitone veronal), TRICINE, TRIS, BICINE, glycylglycine, borate, CHES, ethylamine, glycine-NaOH, CAPS, triethylamine, DEA, BIS, BIS-TRIS, AMP, AMPD (aminomethylpropenediol) or any buffer with a pH over 9. More preferably, suitable buffers include TRIS, DEA, BIS, BIS-TRIS, AMP, or AMPD.

By "charcoal" is meant reagent grade charcoal. Preferably, the charcoal is "activated charcoal" or "active charcoal." The charcoal used in the present invention may also be referred to simply as "carbon" or "activated carbon;" therefore, the terms "charcoal" and "carbon" may be used interchangeably. The charcoal may be purchased as "activated charcoal" or the charcoal may be "activated" prior to use. The charcoal can be a powder of different mesh sizes or in the form of a pellet. Activated charcoal or activated carbon is charcoal or carbon that has been treated with oxygen to open up millions of tiny pores between the carbon atoms. Accordingly, the activated charcoal has a porous internal microstructure having an extremely high surface area. The "activated charcoal" suitable for use herein is reagent grade charcoal. Preferably, the activated charcoal is characterized as having an internal surface area of approximately 400 to 1,200 square meters per gram. Activated carbon can be prepared, for example, by acid.

A "stabilizing amount of charcoal" is that amount of charcoal necessary to provide a solubilized phenyl phosphate with acceptable performance parameters for at least 24 hours at room temperature when exposed to light and more preferably for 30 days or more in light and at room temperature. Acceptable performance parameters include a background absorbance of less than about 0.1 at 405 nm and an activity of about 0.2 OD/min. A stabilizing amount of charcoal allows the phenyl phosphate to react in a colorimetric assay, while preventing non-enzymatic hydrolysis. Preferably a stabilizing amount of charcoal is from about 20 mg charcoal per mL of phenyl phosphate solution or less. More preferably, the amount is about 15 mg charcoal per mL of phenyl phosphate solution or less. Even more preferably, the stabilizing amount of charcoal is about 10 mg/mL+/−5 mg/mL.

By way of example, a stabilizing amount of charcoal is an amount of charcoal necessary to provide a 1.5 g/L phenyl phosphate buffered solution having a pH of greater than 9.0 with a background absorbance of less than about 0.1 and an activity of about 0.2 OD/min for at least 24 hours or more at room temperature and exposed to light. This stabilizing amount of charcoal can be an amount of charcoal retained in the solubilized phenyl phosphate or can be an amount of charcoal contacted with the solubilized phenyl phosphate for a finite period of time and then removed such that substantially all of the charcoal is removed from the solubilized phenyl phosphate.

By "recycling" is meant a method of treating solubilized phenyl phosphate that has turned color due to non-enzymatic hydrolysis. Recycling provides the previously colored, solubilized phenyl phosphate with an absorbance of less than 0.1 OD/min at 405 nm after treatment and an activity of 0.2 OD/min after treatment.

By a "recycling amount of charcoal" is meant that amount of charcoal necessary to provide a previously colored, soublized phenyl phosphate, which has colored due to non-enzymatic hydrolysis, with an absorbance of less than about 0.1 OD/min. A recycling amount of charcoal is about 5 g to about 15 g of charcoal per liter of substrate. More preferably, the amount is about 10 g to about 12.5 g/L but more charcoal may be required for material that has been subjected to long-term hydrolysis (e.g., 30 days or more) when measured at 405 nm and an activity of about 0.2 OD/min after recycling treatment.

By "removing substantially all," it is meant that 75% or higher of the charcoal added is removed, preferably 80% or higher, more preferably 90% or higher, even more preferably 95% or higher, and even more preferably 99% or higher, or any integer value between 80% and 100%.

By "background absorbance" with reference to solubilized phenyl phosphate is meant the absorbance of the solubilized phenyl phosphate when measured at 405 nm in the absence of enzyme. Preferably the background absorbance is less than 0.1. The background absorbance is measured by using a spectrophotometer that has been blanked against purified water.

By "ready-to-use" is meant a form of phenyl phosphate, which is formulated for immediate use in an enzymatic assay and requires no further preparation, dilution or treatment of the solubilized phenyl phosphate.

By "concentrated phenyl phosphate" is meant solubilized phenyl phosphate, which can be diluted prior to use in an enzymatic assay.

By "charcoal untreated soublized phenyl phosphate" is meant a phenyl phosphate buffered solution having a pH of greater than 9.0 that has not previously been exposed to charcoal, and which when exposed to light at room temperature for about 8 hours, the charcoal untreated solubilized phenyl phosphate will undergo non-enzymatic hydrolysis, thus providing a phenyl phosphate solution having an absorbance value over 0.1 when measured at 405 nm and which will be commercially useless. Preferably, the solubilized phenyl phosphate is PNPP in an amount of about 1.0 to about 1.5 g/L PNPP buffered solution having a pH greater than 9.0.

1.2 Abbreviations

The following is a list of commonly accepted scientific abbreviations and corresponding full-length names.

AMP 2-amino-2-methyl-1-propanol
AMPD 2-amino-2-methyl-1,3-propanediol
BICINE N,N-bis(2-hydroxyethyl)glycine
BIS bis(2-hydroxyethyl)imino
BIS-TRIS bis(2-hydroxyethyl)imino-tris(hydroxymethyl)methane or 2[bis-(2-hydroxyethyl)amino]-2-(hydroxymethyl)-propane-1,3-diol
CHES 2-(cyclohexylamino)ethanesulfonic acid
DEA diethylamine
ELISA enzyme linked immunosorbant assay
Gly Gly HCl glycyl glycine hydrochloride
HEPES 4-(2-hydroxyethyl)-1-piperazine-ethanesulfonic acid (or Hepes)
MOPS 3-(N-morpholino)propansesulfonic acid
PNPP paranitrophenylphosphate or p-nitrophenylphosphate
RT room temperature
TES N-tris(hydroxymethyl)methyl-2-aminoethanesulfonic acid)
TRICINE N-tris[(hydroxymethyl)methyl]glycine or N-[2-hydroxy-1,1-bis(hydroxymethyl)-ethyl]glycine
TRIS tris(hydroxymethyl)aminomethane or 2-amino-2-hydroxymethyl-1,3-propanediol or THAM 2. Methods of Preparing and Storing Phenyl Phosphates Prior to the methods and compositions for stabilizing and recycling phenyl phosphate as described herein, ready-to-use phenyl phosphate substrate required special packaging (e.g., amber bottles or other containers which shielded the ready-to-use phenyl phosphate from light) and also required limited shipping and storage conditions (e.g., storage at 4° C., no exposure to temperatures above room temperature but no freezing, shipment overnight). By way of example, when shipping ready-to-use phenyl phosphate, manufacturers had to ship the ready-to-use phenyl phosphate in frozen gel packs or wet ice in an appropriate shipping container, both of which are significantly more expensive than shipping the item at ambient or room temperature. Additionally, there was no guarantee that phenyl phosphate shipments would not be exposed to excessive heat if shipped during the summer months. In addition, when using ready-to-use phenyl phosphate, the shelf-life rapidly decreased due to exposure of the phenyl phosphate to light and temperatures above 4° C. when on the laboratory benchtop. Even when using phenyl phosphate in amber containers, (i.e., K-Gold® Substrate), it is still recommended that the phenyl phosphate substrate in the amber container be stored at 4° C. and in actual use, it has limited stability to non-enzymatic hydrolysis.

The methods of preparing ready-to-use phenyl phosphate, as described herein, do not require the use of amber bottles and/or refrigeration for shipping and/or storage. Refrigeration and/or use of light inhibiting bottles, such as amber bottles, can be used with the compositions and kits disclosed herein for even further increasing the already surprisingly lengthy shelf-life of the ready-to-use phenyl phosphate substrates described herein.

For example, solubilized PNPP can be prepared by solubilizing PNPP in any basic buffer. Preferably, the solubilized PNPP is an aqueous buffered solution having a pH of greater than approximately 9.0. Preferably, the solubilized PNPP has a concentration of approximately 2.0 g/L or less phenyl phosphate. However, the solubilized PNPP may also be prepared in a concentrated form, e.g., about 3.0 g/L PNPP.

The solubilized phenyl phosphate is contacted with a stabilizing amount of charcoal to stabilize the solubilized phenyl phosphate. A stabilizing amount of charcoal is that amount of charcoal necessary to provide a solubilized phenyl phosphate with acceptable performance parameters for at least 24 hours at room temperature (more preferably stable for 30 days or more) when exposed to light. Acceptable performance parameters include a background absorbance of less than about 0.1 at 405 nm and an activity of about 0.2 OD/min. Preferably a stabilizing amount of charcoal is from about 20 mg charcoal per mL of phenyl phosphate solution or less. More preferably, the amount is about 15 mg charcoal per mL of phenyl phosphate solution or less. Even more preferably, the stabilizing amount of charcoal is about 10 mg/mL+/−5 mg/mL.

Contacting solubilized PNPP with charcoal or charcoal treatment can be performed by any suitable means. These means include, but are not limited to, (1) contacting the solubilized phenyl phosphate with charcoal and retaining the charcoal in the solubilized phenyl phosphate (i.e., constant contact);

(2) contacting the solubilized phenyl phosphate with charcoal for a finite period of time (e.g., 5 minutes to 48 hours and any length of time in between) followed by removing the charcoal from the solubilized phenyl phosphate; and (3) exposing the solubilized phenyl phosphate to charcoal, wherein the charcoal is in a dialysis receptacle or other receptacle in the container which holds the solubilized phenyl phosphate.

For constant contact of the solubilized phenyl phosphate with charcoal, it is contemplated that charcoal can be added to the solubilized phenyl phosphate; the charcoal can be in the form of pellets, granulated charcoal, powdered charcoal and the like. In addition, for constant contact, the charcoal can be adhered to the packaging device containing the phenyl phosphate (e.g., adhered to the bottle containing the ready-to-use phenyl phosphate). The charcoal can be adhered to the mouth of the bottle through which the phenyl phosphate is poured, adhered to at least a portion of the sides of the bottle, and/or adhered to the bottom of the bottle.

When contacting the solubilized phenyl phosphate with charcoal for a finite period of time, the solubilized phenyl phosphate is maintained in contact with the charcoal for about 60 minutes or longer, preferably about 60 minutes to about 8 hours, and even more preferably about 60 minutes to overnight. After the period of contact, substantially all of the charcoal is removed from the solubilized phenyl phosphate by any means suitable for removing the charcoal from the solution. The means for removing the charcoal will be dependent upon the form of charcoal used. Suitable means of removing the charcoal will be recognized by those skilled in the art. By way of example, for removing granulated, pellets, or powdered charcoal, the solubilized phenyl phosphate may be pipetted off of the charcoal after it has been allowed to settle to the bottom of the container, by chemical extraction (e.g., use of mineral oil) the solubilized phenyl phosphate may be filtered to remove substantially all of the charcoal, the charcoal may also be centrifuged to a pellet and then removed or can be removed by any suitable means known in the art.

In addition, the charcoal can be contained within a device that is added to the solubilized phenyl phosphate. This device will contain the charcoal and allow it to be exposed to the solubilized phenyl phosphate. Such devices include, for example, perforated capsules, blister packs, and sachets. Other mechanisms, which permit exposure or contact of solubilized phenyl phosphate with charcoal are also contemplated and included within the present invention.

Solubilized phenyl phosphate, which has colored due to non-enzymatic hydrolysis rendering it commercially useless may be recycled through the use of a recycling amount of charcoal. To recycle solubilized phenyl phosphate that has colored, the solubilized phenyl phosphate is contacted with charcoal to provide solubilized phenyl phosphate having acceptable activity and background absorbance. By contacting a solubilized phenyl phosphate, which has colored due to non-enzymatic hydrolysis, with charcoal, the previously colored, solubilized phenyl phosphate can be provided with acceptable background absorbance and acceptable activity for use in enzyme assays. Contacting colored solubilized phenyl phosphate with charcoal or charcoal treatment can be performed by any suitable means. These means include, but are not limited to, the methods as described above for a solubilized phenyl phosphate that has not previously colored.

Treatment of previously colored, solubilized phenyl phosphate is preferably done with about 15 mg of charcoal per mL of phenyl phosphate. or less for a period of about 5 minutes to 48 hours or more (i.e., treatment can be constant until use of the solubilized phenyl phosphate in an enzymatic assay). More preferably, the solubilized phenyl phosphate is treated with charcoal for about 3 hours to overnight.

Even more preferably, the solubilized phenyl phosphate is treated overnight with 10 mg/mL+/−5 mg/mL charcoal. As above with solubilized phenyl phosphate that has not previously colored, the charcoal can be in any form including, for example, pellets, powder, granules or other commercially available forms of charcoal and activated charcoal.

2.1 Buffers for Solubilizing Phenyl Phosphate

Preferably the solubilized phenyl phosphate is an aqueous buffered solution having a pH of approximately 9.0 or greater. According to the present invention, any basic buffer can be used to solubilize phenyl phosphate as long as it is functional in the enzymatic assay. Preferred buffers include, but are not limited to, AMP, AMPD, BIS, BIS-TRIS, TRIS, and DEA. Methods of preparing these buffers are known to those of skill in the art.

For example, if the solubilized phenyl phosphate is solubilized PNPP, it is in a buffered solution comprising about 2.0 g or less PNPP per liter of buffer and more preferably 1.0 to 1.5 g/L PNPP.

2.2 Charcoal

The charcoal used in the present invention to stabilize and/or recycle solubilized phenyl phosphate is reagent grade charcoal. Preferably the charcoal is "activated charcoal" or "active charcoal." The charcoal used in the present invention may also be referred to simply as "carbon" or "activated carbon;" therefore, the terms "charcoal" and "carbon" may be used interchangeably. The charcoal may be purchased as "activated charcoal" or the charcoal may be "activated" prior to use.

Activated charcoal or activated carbon is charcoal or carbon that has been treated with oxygen to open up millions of tiny pores between the carbon atoms. Accordingly, the activated charcoal has a porous internal microstructure having an extremely high surface area. The "activated charcoal" suitable for use herein is reagent grade charcoal. Preferably, the activated charcoal is characterized as having an internal surface area of approximately 400 to 1,200 square meters per gram. Activated carbon can be prepared, for example, by acid treatment or other methods for activating charcoal.

Any commercially available charcoal that is activated or unactivated and is reagent grade can be used to treat the solubilized phenyl phosphate. Activated charcoal may be commercially obtained or the charcoal may be obtained and activated according to methods well known to those of skill in the art. Activated carbon can be prepared, for example, by acid treatment or other activation means.

By way of example, charcoal can be activated as follows:
850 mL $H_2O$ and 150 mL 12 N HCl are admixed to provide an acidic solution for activating the charcoal.
The acidic solution is added to 200 g charcoal and the charcoal is activated over 3 hours.
The activated charcoal is rinsed in reverse osmosis (RO), deionized or water of comparable quantity RO $H_2O$ excess, 2 to 3 times.
The charcoal air-dried overnight and then the charcoal is dried at 37 C over a second night.

According to the present invention, charcoal is added to solubilized phenyl phosphate in a stabilizing or recycling amount. Preferably, the charcoal is added in an amount of approximately 5 to 15 mg/mL, and even more preferably in an amount of approximately 10 mg/mL. The solubilized phenyl phosphate may be stabilized by contacting the phenyl phosphate with charcoal and maintaining the solubilized phenyl phosphate in contact with the charcoal. In the alternative, the solubilized phenyl phosphate may be contacted with the charcoal for a sufficient time to stabilize or recycle the phenyl phosphate (e.g., overnight) and then substantially all of the charcoal may be removed from the solubilized phenyl phosphate.

3. Packaging for Kits and Ready-to-Use Phenyl Phosphate

Ready-to-use forms of phenyl phosphate or concentrated solubilized phenyl phosphate are packaged in shipping containers sufficient to prevent breakage or leakage of the solubilized phenyl phosphate; however, there are no refrigeration or limitations on storage conditions that are required for shipping and storing solubilized phenyl phosphate stabilized according to the present invention.

The ready-to-use and concentrated forms of phenyl phosphate can be placed in any air tight container suitable for a liquid, including but not limited to glass, plastic, amber colored or clear, containers and the like. According to the present invention, solubilized phenyl phosphate contacted with charcoal does not require light-inhibiting, air-tight containers suitable for liquids, merely containers suitable for liquids are needed.

For ready-to-use and concentrated, solubilized phenyl phosphate the air-tight, liquid suitable container can be coated on the inside of the container with charcoal in a stabilizing amount. For example, charcoal can be adhered to a surface of the container that comes in contact with the solubilized phenyl phosphate. By way of example, the charcoal can be adhered to the mouth of the container, the sides of the container, the bottom of the container, and combinations thereof. The methods of adhering the charcoal to the container are known to those of skill in the art. The method of adhering the charcoal should not render the charcoal inactive and should not destabilize the solubilized phenyl phosphate.

Alternatively, the ready-to-use and concentrated, solubilized forms of phenyl phosphate can be shipped in containers that have a device or other means to expose the solubilized phenyl phosphate to charcoal. Such devices or other means can include charcoal covered magnetic stir bars, sachets containing charcoal, charcoal contained in an osmotic membrane in the vessel containing the solubilized phenyl phosphate, charcoal contained in porous capsules, charcoal in a container which allows it to have contact with the solubilized forms of phenyl phosphate and which can be, for example, easy to remove from the solubilized phenyl phosphate containing vessel. The charcoal may also be added directed to the ready-to-use and concentrated, solubilized phenyl phosphate in the form of pellets, granules, powder, and the like.

The solubilized phenyl phosphate in the containers may be maintained in contact with the charcoal. In the alternative, the solubilized phenyl phosphate may be contacted with the charcoal for an adequate time to stabilize the solubilized phenyl phosphate and then substantially all of the charcoal may be removed prior to sealing the solubilized phenyl phosphate in the container.

4. Phenyl Phosphate Kits

Kits comprising stabilized phenyl phosphate according to the present invention are contemplated. These kits comprise solubilized phenyl phosphate, which has been either pretreated with charcoal, as described herein, or wherein the solubilized phenyl phosphate is in constant contact with charcoal. In an additional embodiment, the phenyl phosphate may be untreated and the kit may further comprise a phenyl phosphate recycling kit.

These kits may be appropriate for an enzyme activity assay, for example, for alkaline phosphatase-phenyl phosphate reactions or acid phosphatase-phenyl phosphate reactions. Accordingly, the kits may further comprise appropriate enzymes, i.e., alkaline phosphatase or acid phosphatase.

The kits according to the present invention may also include kits for phenyl phosphate recycling. The recycling kits are appropriate for recycling phenyl phosphate colored due to non-enzymatic hydrolysis. Solubilized phenyl phosphate colored due to non-enzymatic hydrolysis exhibits an absorbance over 0.1 OD/min when measured at 405 nm. The kits for recycling the previously colored phenyl phosphate comprise an amount of charcoal sufficient to recycle the solubilized phenyl phosphate that has previously colored due to non-enzymatic hydrolysis, i.e., a recycling amount of charcoal.

The amount of charcoal to recycle the solubilized phenyl phosphate is an amount such that approximately 10 mg/mL+/−5 mg/mL can be added to solubilized phenyl phosphate. Preferably, the charcoal is in self-contained units of approximately 100 mg charcoal. Accordingly, these self-contained units can be added as necessary to solubilized phenyl phosphate in need of recycling. The self-contained units are added as necessary to achieve approximately 10 mg/mL+/−5 mg/mL of charcoal per solubilized phenyl phosphate. By way of example, one self contained unit would be added 10 mL of solubilized phenyl phosphate.

The charcoal may be maintained in constant contact with the previously colored, solubilized phenyl phosphate or the charcoal may be contacted with the solubilized phenyl phosphate and then removed after a sufficient time, for example, overnight. After contact with the charcoal, the previously colored, solubilized phenyl phosphate exhibits acceptable background absorbance (i.e., less than 0.1 at 405 nm) and acceptable activity (0.2 OD/min or more) when exposed to enzyme.

5. Recycling Phenyl Phosphates

Another aspect of the invention is to recycle solubilized phenyl phosphate previously colored due to non-enzymatic hydrolysis. After a solution of phenyl phosphate colors due to non-enzymatic hydrolysis, it is no longer capable of being used to detect enzyme activity. The previously colored, solubilized phenyl phosphates are commercially worthless. The previously colored, solubilized phenyl phosphate may result from storage problems experienced during shipping (e.g., excessive heat) and may also result from storage during use on the bench-top. The previously colored, solubilized phenyl phosphate results from non-enzymatic hydrolysis that occurs when the solubilized phenyl phosphate is exposed to light, is exposed to room temperature, is stored long-term even at 4° C., and combinations thereof. The solubilized phenyl phosphate previously colored due to non-enzymatic hydrolysis can be treated using the methods and materials described herein to recycle the otherwise commercially worthless solublized phenyl phosphate. After recycling, the solubilized phenyl phosphate exhibits acceptable background absorbance and acceptable activity.

Another aspect of the invention contemplates the use of kits, which can be part of a kit appropriate for an enzyme activity assay, to recycle solubilized phenyl phosphate that has colored due to non-enzymatic hydrolysis. By way of example, a ready-to-use phenyl phosphate, which was not treated with charcoal, will color due to non-enzymatic hydrolysis if stored in a clear container on the bench-top at room temperature for several hours. After coloring, the phenyl phosphate is no longer useful in an enzymatic assay due to an unacceptably high background. Using a recycling kit according to the present invention, the phenyl phosphate colored due to non-enzymatic hydrolysis may be recycled to a solubilized phenyl phosphate with acceptable background absorbance (i.e., less than 0.1) and acceptable activity (0.2 OD/min or more). The recycling kit may be made commercially available separately, available as part of the original ready-to-use phenyl phosphate kit, available as a part of the original kit for assaying enzyme activity, or combinations thereof.

Such recycling kits include an amount of charcoal sufficient to recycle the solubilized phenyl phosphate that has previously colored due to non-enzymatic hydrolysis, i.e., a recycling amount of charcoal.

The amount of charcoal to recycle the solubilized phenyl phosphate is an amount such that approximately 10 mg/mL+/−5 mg/mL charcoal is added to solubilized phenyl phosphate. When available as part of a kit, preferably, the charcoal is in self-contained units of approximately 100 mg charcoal. Accordingly, these self-contained units can be added as necessary to solubilized phenyl phosphate in need of recycling. The self-contained units are added as necessary to achieve approximately 10 mg/mL+/−5 mg/mL of charcoal per solubilized phenyl phosphate. By way of example, one self contained unit would be added 10 mL of solubilized phenyl phosphate.

To recycle solubilized phenyl phosphate, the charcoal may be maintained in constant contact with the previously colored, solubilized phenyl phosphate or the charcoal may be contacted with the solubilized phenyl phosphate and then removed after a sufficient time, for example, overnight. After contact with the charcoal, the previously colored, solubilized phenyl phosphate exhibits acceptable background absorbance (i.e., less than 0.1) and acceptable activity (e.g., 0.2 OD/min or more) when exposed to enzyme.

More preferably, the charcoal in a recycling kit may be in a form that is reusable (e.g., charcoal in a sachet containment device such as dialysis tubing). By way of example, a recycling kit, as described herein, may contain a recycling amount of charcoal, a containment means for the recycling amount of charcoal (e.g., sachet, a sealed package which can be opened and the charcoal contents placed into the solubilized phenyl phosphate, a dialysis tube or other dialysis material in the form of a containment device). In the alternative, the recycling kit may contain a device to which the charcoal is adhered and which can be placed in contact with the solubilized, previously colored phenyl phosphate (e.g., a magnetic stirrer with charcoal adhered to its surface, a bottle to which charcoal is adhered to an interior surface and the like).

It is important to note that the methods and kits of the present invention may be used to recycle solubilized phenyl phosphate that has previously colored due to non-enzymatic hydrolysis. In recycling the solubilized, previously colored phenyl phosphate, the solubilized phenyl phosphate is returned to acceptable background absorbance and acceptable activity. When the methods and kits of the present invention are used with solubilized phenyl phosphate that has colored due to enzymatic hydrolysis, it has been surprisingly discovered that the phenyl phosphate is not returned to acceptable activity. Accordingly, the methods and kits of the present invention are surprisingly useful for recycling solubilized phenyl phosphate that has colored due to non-enzymatic hydrolysis.

6. Assay Use of Phenyl Phosphate as a Substrate

Solubilized phenyl phosphate is commonly used in combination with phosphatase enzymes. Solubilized phenyl phosphate may be used with the phosphatase enzymes as a substrate since phenyl phosphate contains hydrolyzable phosphoric esters that can readily be used to measure phosphatase activity. In particular, the phosphatase enzymes hydrolyze the solubilized phenyl phosphate, the substrate, to an end-product that is colored end product in basic solution. Solubilized phenyl phosphate also typically contains a magnesium compound that releases magnesium ions into the solution.

The rate of hydrolysis of the solubilized phenyl phosphate substrate can be determined by following the increase in absorbance at approximately 405 nm, i.e., by measuring the rate of formation of the colored end-product. Measurement of the increase in absorbance due to the colored p-nitrophenoxide produced by reaction with the phosphatase enzymes in a given time frame provides an accurate determination of the amount of analyte present. The rate of color formation, which is indicative of the rate of hydrolysis may be measured over time (i.e., when using the enzyme alkaline phosphatase) or can be read as an end point assay (i.e., when using the enzyme acid phosphatase).

It is essential that the solubilized phenyl phosphate have an acceptable background absorbance so that the rate of color formation can be measured. If the background absorbance is too high, the assay will not be sensitive enough to detect a measurable amount of color formation. Acceptable background absorbances are preferably 0.1 or less when measured at 405 nm.

It is also essential that the solubilized phenyl phosphate retain acceptable activity so that it will hydrolyze in the presence of the phosphatase enzymes to provide a measurable rate of color formation. The absorbance may be read for 2 to 3 minutes determining the rate of increase over the linear portion of the curve. It may be necessary to further dilute the enzyme if the absorbance exceeds 1.5 during a 2-minute incubation. In the alternative, the color formation may be read as an end point assay, for example, when using the enzyme acid phosphatase since it is necessary to measure the color formation in a solution buffered to basic pH. Acceptable activities for solubilized phenyl phosphate are preferably 0.2 OD/min or more.

The solubilized phenyl phosphate stabilized according to the present invention exhibits both acceptable background absorbance and acceptable activity for use in enzyme assays, in particular phosphatase assays.

Although the present invention has been described in detail with reference to examples below, it is understood that various modifications can be made without departing from the spirit of the invention, and would be readily known to the skilled artisan.

EXAMPLES

Example 1

Charcoal Stabilization of PNPP at Room Temperature

PNPP Buffer lot 0110602 was pH adjusted to 9.80 from 9.75. PNPP was added to the buffer in amounts of 1.5 g or 3.0 g per liter and admixed. PNPP from Sigma (S), NBC (N) and Biosynth (B) were used. 10 g/L of activated charcoal was then added to each of the samples. The lots were allowed to remain at room temperature and subjected to room lighting.

TABLE I

| S 1.5 g/L (#1) | S 3.0 g/L (#2) | N. 1.5 g/L (#3) | N 3.0 g/L (#4) | B 3.0 g/L (#5) |
|---|---|---|---|---|
| 1.5 g PNPP Sigma Lot 61K5003 | 3.0 g PNPP Sigma Lot 61K5003 | 1.5 g PNPP NBC Lot GF26A | 3.0 g PNPP NBC Lot GF26A | 3.0 g old PNPP Biosynth Lot 15128/1 |
| Add 10 g charcoal | Add 10 g charcoal | Add 10 g charcoal | Add 10 g charcoal | Add 10 g charcoal |
| Mix 2 hrs | Mix 2 hrs | Mix 2 hrs | Mix 2 hrs | Mix 2 hrs |
| $A_{405} = 0.048$ | $A_{405} = 0.082$ | $A_{405} = 0.047$ | $A_{405} = 0.092$ | $A_{405} = 0.112$ |
| $A_{310} = 0.450$ | $A_{310} = 1.511$ | $A_{310} = 0.477$ | $A_{310} = 1.589$ | $A_{310} = 2.107$ |
| AA = 0.253 | AA = 0.277 | AA = 0.256 | AA = 0.275 | AA = 0.280 |

A concentration of 3.0 g/L of PNPP is well above what is normally solubilized, as this concentration of PNPP typically rapidly forms the colored quinoid form of PNPP. Nevertheless, even at room temperature and exposed to light, the samples, including the 3.0 g/L samples, remained clear exhibiting an acceptable background absorbance of less than 0.1 at 405 nm.

Example 2

Long Term Stability of Charcoal Treated Solubilized PNPP 30 mL of each batch from Example 1 was removed from the original batches and placed into clear Nalgene bottles in the absence of charcoal. The samples were stored in a refrigerator at 4° C. These samples were maintained under these conditions for two years. After storage for two years, the samples exhibited an absorbance of less than 0.1 when measured at 405 nm.

After storage for two years, these samples were then placed in light at 37 C for 2 days. Even after 2 days, when tested at 400–410 nm, the samples surprisingly and unexpectedly had absorbance values of less than 0.1 OD/min for the 1.0, 1.5 and 3.0 g/L PNPP.

Example 3

Charcoal Stabilization of PNPP at Room Temperature

Additional 30 mL batches were taken from the batches Example 1 and mixed for 1 hour at room temperature in light in the clear Nalgene bottles. Aliquots from each of these batches were then allowed to sit on the bench-top at room temperature. 50 µL were taken from the samples at day 3, 4, 5, 7, and 10, and at day 10 a sample was taken and stored for an additional 2 days at 37° C. after which a 50 µL sample was taken. The 50 µL samples were tested for absorbance to determine the stability of the samples during storage for a period of time. The 50 µL samples were brought to 1 mL with water, and a spectrophotometric UV scan of 295 to 410 nm was performed to assess the quality of the raw material. Accordingly, absorbance was recorded as summarized in Table II below for the samples after storage at days 3, 4, 5, 7, 10 and 10 days at room temperature with an additional 2 days at 37° C. Table II below summarizes the values obtained at 310 nm absorbance.

TABLE II

| Day | Batch #1 | Batch #2 | Batch #3 | Batch #4 | Batch #5 |
|---|---|---|---|---|---|
| 3 | 0.468 | 1.517 | 0.476 | 1.618 | 2.097 |
| 4 | 0.457 | 1.478 | 0.490 | 1.601 | 2.084 |
| 5 | 0.469 | 1.511 | 0.490 | 1.578 | 2.066 |

TABLE II-continued

| Day | Batch #1 | Batch #2 | Batch #3 | Batch #4 | Batch #5 |
|---|---|---|---|---|---|
| 7 | 0.444 | 1.499 | 0.477 | 1.578 | 2.029 |
| 10 | 0.470 | 1.490 | 0.513 | 1.617 | 2.051 |
| 10@37° C. | 0.605 | 1.545 | 0.626 | 1.615 | 2.067 |

Background absorbance at 405 nm was recorded as summarized in Table III below for the samples after storage at the days as specified in the Table.

TABLE III

| Day | Batch #1 S 1.5 g/L | Batch #2 S 3.0 g/L | Batch #3 N 1.5 g/L | Batch #4 N 3.0 g/L | Batch #5 B 3.0 g/L |
|---|---|---|---|---|---|
| Day 0 | 0.048 | 0.082 | 0.047 | 0.092 | 0.122 |
| 4 | 0.082 | 0.140 | 0.147 | 0.137 | 0.166 |
| 5 | 0.075 | 0.086 | 0.049 | 0.089 | 0.121 |
| 7 | 0.038 | 0.079 | 0.041 | 0.078 | 0.100 |
| 10 | 0.025 | 0.075 | 0.031 | 0.079 | 0.101 |
| 10 (w/additional 2 days at 37° C.) | 0.039 | 0.089 | 0.036 | 0.097 | 0.116 |
| 11 | 0.050 | 0.130 | 0.050 | 0.164 | 0.164 |
| 11 @RT | 0.026 | 0.075 | 0.027 | 0.078 | 0.097 |
| 3 @37° C. | 0.042 | 0.091 | 0.049 | 0.102 | 0.141 |
| 7 @37° C. | — | 0.078 | — | — | — |

S = Sigma;
N = NBC;
B = Biosynth

These charcoal treated samples were then tested for activity in the presence of alkaline phosphatase. To test the activity, the enzyme was added to the charcoal treated samples at a concentration of 10 μL enzyme per milliliter substrate. The rate of color generation was determined at ambient temperature. Absorbance was measured at 405 nm with the results as summarized in Table IV below obtained for each of the five batches.

TABLE IV

| Time | Batch #1 | Batch #2 | Batch #3 | Batch #4 | Batch #5 |
|---|---|---|---|---|---|
| Day 0 | 0.253 | 0.277 | 0.256 | 0.275 | 0.280 |
| Day 4 | 0.202 | 0.208 | 0.182 | 0.217 | 0.266 |
| Day 5 | 0.213 | 0.278 | 0.258 | 0.274 | 0.277 |
| Day 7 | 0.252 | 0.279 | 0.255 | 0.274 | 0.281 |
| Day 10 | 0.261 | 0.274 | 0.265 | 0.275 | 0.274 |
| Day 10 w/additional 2 days at 37° C. | 0.258 | 0.267 | 0.262 | 0.269 | 0.275 |
| Day 11 (after day 10 stored at 37° C. overnight w/no charcoal) | 0.249 | 0.264 | 0.260 | 0.262 | 0.269 |
| Day 11 RT | 0.259 | 0.274 | 0.257 | 0.274 | 0.279 |
| Day 10 w/additional 3 days at 37° C. | 0.222 | 0.245 | 0.233 | 0.255 | 0.265 |

Example 4

Charcoal Stabilization of PNPP at 4° C.

A sample for each of the days as tested above in Example 3 was removed from the sample batches and was placed into clear Nalgene bottles in the absence of charcoal. The samples were stored in a refrigerator at 4° C. These samples were maintained under these conditions for two years.

These samples which had been treated with charcoal and then had the charcoal removed from the solution two years previously (i.e., charcoal pellets had been removed but the samples were not filtered, such that charcoal shards may have remained in the solution) were stored as described above. The treatment with charcoal was from overnight to just prior to use depending on when the sample was taken according to Example 3, whereupon the sample was removed from contact with charcoal. The samples were then stored under refrigeration at approximately 4° C. for two years. After storage for two years in a refrigerator at 4° C., the samples exhibited an absorbance of less than 0.1 when measured at 405 nm.

These samples (at 1.0, 1.5 or 3.0 g/L) were then placed in light at 37° C. for 2 days. Even after 2 days, when tested at 405 nm, the samples surprisingly and unexpectedly had absorbance values of less than 0.1.

Example 5

PNPP in AMPD Buffer

The following concentrations of PNPP were prepared in AMPD buffer. The solutions were admixed for 4 hours protected from light at room temperature. The solutions were then stored at 4° C. overnight. The solutions as prepared are summarized below in Table V.

TABLE V

| 0.5 g AMPD | 0.5 g AMPD | 1.0 g AMPD | 1.0 g AMPD |
|---|---|---|---|
| 1.0 PNPP | 2.0 g PNPP | 0.5 g PNPP | 2 g PNPP |
| (100 mg/mL) | (200 mg/mL) | (50 mg/mL) | (200 mg/mL) |
| 10 mL $H_2O$ | 10 mL $H_2O$ | 10 mL $H_2O$ | 10 mL $H_2O$ |
| 1 g charcoal | 1 g charcoal | 1 g charcoal | 1 g charcoal |

After storage overnight, the samples of the solutions were tested for background absorbance at 405 nm and all exhibited acceptable absorbances (i.e., less than 0.1).

Example 6

Charcoal Filtered Samples

A sample of 1.5 g/L PNPP in AMP had charcoal in the amount of 10 mg/mL added and admixed. The solubilized PNPP sample was left in contact with the charcoal for at least one hour and was then filtered to remove the charcoal, placed in a Nalgene bottle, in a lighted room at room temperature overnight. The solubilized PNPP remained clear overnight.

The same experiment was performed using 3.0 g/L PNPP. The activity was similar to what was observed with the 1.5 g/L amount, however there was increased background over time, as expected.

Example 7

Recycled PNPP

Samples of PNPP (i.e., 1.5 g/L) in AMP and AMPD buffers were allowed to turn color due to non-enzymatic hydrolysis by placing the charcoal-untreated samples at room temperature in light for several hours. The absorbance of the colored, solubilized PNPP was measured at 405 nm and was found to be 2.8.

10 mg/ml charcoal was then added to the samples for 5 to 20 minutes at which time the absorbance was again tested. The absorbance of the previously colored solubilized PNPP exhibited values of less than 0.1 when measured at 405 nm after contact with the charcoal. These samples were then tested with enzyme and found to have assay acceptable activity (0.2 OD/min or more) similar to that of solubilized PNPP that had not previously colored due to non-enzymatic hydrolysis.

Comparative Example 8

Enzyme Treatment of PNPP

As a comparative example, a sample of PNPP (1.5 g/L PNPP in a DEA Buffer) was subjected to enzymatic hydrolysis in the presence of alkaline phosphatase. Assays, such as ELISAs, use alkaline phosphatase and the substrate, PNPP as a means of testing for the presence of a compound (e.g., a polypeptide that is coupled to the substrate). Typically the PNPP is present in the assay in concentrations that are in excess to the enzyme. Accordingly, samples of solubilized PNPP with absorbances less than 0.1 when tested at 405 nm, were exposed to alkaline phosphatase.

The enzyme (i.e., alkaline phosphatase) was added to the samples at a concentration of 10 μL enzyme per milliliter substrate. The sample of PNPP was colored due to the enzymatic hydrolysis. 10 mg/mL charcoal was then added to the samples for 5 to 20 minutes at which time the absorbance was again tested. The absorbance of the previously colored, solubilized PNPP was greater than 2.0 OD when measured at 405 nm after contact with the charcoal. As may be expected, the charcoal removed color from the enzyme reacted samples. However, surprisingly, these samples were then tested with enzyme for activity and found to have assay activity of less than 0.1 OD/min. Accordingly, the charcoal treatment did not provide the solubilized PNPP colored due to enzymatic hydrolysis with acceptable activity.

Therefore, the enzyme-reacted samples of solubilized PNPP after a treatment with charcoal were clear, but had no measurable functional PNPP substrate, which could be detected using the second enzymatic reaction. The unexpected conclusion from this data is that the active form of PNPP is no longer present in a detectable manner after enzymatic reaction even when treated under recycling conditions according to the present invention.

While the invention has been described in detail and with reference to specific embodiments thereof, it will be apparent to one skilled in the art that various changes and modifications can be made without departing from the spirit and scope thereof.

What is claimed is:

1. A kit for phosphatase-phenyl phosphate reactions comprising separately (i) a phosphatase and (ii) a stabilized, colorless solubilized phenyl phosphate, wherein the stabilized, colorless solubilized phenyl phosphate comprises phenyl phosphate, a buffer, and charcoal.

2. The kit of claim 1, wherein the phosphatase is alkaline phosphatase or acid phosphatase.

3. The kit of claim 1, wherein the phenyl phosphate is paranitrophenyl phosphate.

4. The kit of claim 3, wherein the solubilized phenyl phosphate comprises $\leq 3.0$ g/L paranitrophenyl phosphate.

5. The kit of claim 3, wherein the solubilized phenyl phosphate comprises approximately 1.0 to 3.0 g/L paranitrophenyl phosphate.

6. The kit of claim 3, wherein the solubilized phenyl phosphate comprises approximately 1.5 g/L paranitrophenyl phosphate.

7. The kit of claim 1, wherein the buffer has a pH of greater than approximately 9.0.

8. The kit of claim 1, wherein the buffer is a basic buffer.

9. The kit of claim 8, wherein the basic buffer is DEA, BIS-TRIS, TRIS, AMP, or AMPD.

10. The kit of claim 1, wherein the charcoal is activated charcoal.

11. The kit of claim 1, wherein the solubilized phenyl phosphate comprises approximately 5 to 15 mg/mL charcoal.

12. The kit of claim 11, wherein the solubilized phenyl phosphate comprises approximately 10 mg/mL charcoal.

13. The kit of claim 1, wherein the phenyl phosphate is a $Na^+$ salt, a $NH^{4+}$ salt, a $Mg^{+2}$ salt or an isomer of a phenyl phosphate.

14. The kit of claim 1, wherein the stabilized, colorless solubilized phenyl phosphate further comprises a magnesium compound.

15. The kit of claim 1, wherein the stabilized, colorless solubilized phenyl phosphate has a background absorbance of less than about 0.1 at 405 nm and an activity of about 0.2 OD/min.

16. The kit of claim 15, wherein the stabilized, colorless solubilized phenyl phosphate has a background absorbance of less than about 0.1 at 405 nm and an activity of about 0.2 OD/min for 30 days or more in light at room temperature.

17. A kit for recycling a solubilized phenyl phosphate having an absorbance over 0.1 OD due to non-enzymatic hydrolysis when measured at 400 to 410 nm comprising a solubilized phenyl phosphate which has been colored due to non-enzymatic hydrolysis and a stabilizing amount of charcoal.

18. The kit of claim 17, wherein the stabilizing amount of charcoal is in an amount of about 10 mg/mL +/−5 mg/mL.

19. The kit of claim 17, wherein the phenyl phosphate is paranitrophenyl phosphate.

20. The kit of claim 19, wherein the charcoal is in self-contained units of about 100 mg charcoal per self-contained unit, and wherein the self-contained units are to be added to the solubilized phenyl phosphate in need of recycling in an amount sufficient to provide about 10+/−5 mg charcoal/mL solubilized phenyl phosphate.

21. The kit of claim 20, wherein the self-contained unit of charcoal is in the form of a pellet, a tablet, a tablet in a blister pack, or a perforated capsule.

* * * * *